(12) United States Patent
Pecina et al.

(10) Patent No.: US 8,532,952 B2
(45) Date of Patent: Sep. 10, 2013

(54) PROCESSES TO CREATE DISCRETE CORROSION DEFECTS ON SUBSTRATES AND ESTABLISH CORROSION NDI TEST STANDARDS

(75) Inventors: Joseph Pecina, Redington Beach, FL (US); Scott Ryan, Saint Petersburg, FL (US); John Cargill, Hobe Sound, FL (US)

(73) Assignee: Concurrent Technologies Corporation, Johnstown, PA (US)

(*) Notice: Subject to any disclaimer, the term of this patent is extended or adjusted under 35 U.S.C. 154(b) by 489 days.

(21) Appl. No.: 12/818,437

(22) Filed: Jun. 18, 2010

(65) Prior Publication Data

US 2010/0288031 A1 Nov. 18, 2010

Related U.S. Application Data

(62) Division of application No. 11/713,886, filed on Mar. 5, 2007, now Pat. No. 7,776,606.

(60) Provisional application No. 60/779,265, filed on Mar. 3, 2006.

(51) Int. Cl.
*G01N 17/00* (2006.01)
*G01N 33/20* (2006.01)

(52) U.S. Cl.
USPC .......... 702/116; 73/86; 73/150 R; 250/252.1; 324/202; 374/1; 378/207; 436/19; 702/182

(58) Field of Classification Search
CPC ................. G01N 17/00; G01N 33/20
USPC .......... 204/401, 404; 205/776.5; 250/252.1, 250/339.01, 341.5; 324/202, 225, 601–602, 324/605–606; 374/1, 4, 7; 378/207; 422/53, 422/119; 436/6, 8, 19; 702/34, 81–82, 116, 702/182; 73/1.01, 1.86, 86, 150 R See application file for complete search history.

(56) References Cited

U.S. PATENT DOCUMENTS

| | | | | |
|---|---|---|---|---|
| 2,770,773 | A | * | 11/1956 | Cooley .......................... 324/221 |
| 5,142,230 | A | * | 8/1992 | Nottingham .................. 324/262 |
| 6,285,183 | B1 | * | 9/2001 | Collingwood et al. ....... 324/202 |
| 6,495,833 | B1 | | 12/2002 | Alfano et al. |
| 7,145,148 | B2 | | 12/2006 | Alfano et al. |
| 2003/0025497 | A1 | * | 2/2003 | Collingwood et al. |
| 2003/0038628 | A1 | * | 2/2003 | Nath et al. ..................... 324/230 |
| 2005/0263704 | A1 | * | 12/2005 | Shelley et al. ........... 250/339.01 |
| 2010/0288032 | A1 | * | 11/2010 | Pecina et al. ........................ 73/86 |

FOREIGN PATENT DOCUMENTS

| | | | |
|---|---|---|---|
| DE | 4113271 | A1 * | 12/1992 |
| EP | 1106986 | A2 | 6/2001 |
| JP | 06018470 | | 1/1994 |
| JP | 10227730 | | 8/1998 |
| JP | 2003188494 | | 7/2003 |

\* cited by examiner

*Primary Examiner* — Thomas P Noland
(74) *Attorney, Agent, or Firm* — Buchanan Ingersoll & Rooney PC

(57) ABSTRACT

Methods and apparatuses are provided for creation of discrete corrosion defects with a wide range of diameter to depth aspect ratios for painted test standards. Also provided are methods for use of those test standards to characterize the corrosion under paint detection threshold, statistical reliability, and accuracy of NDI and/or NDT techniques including but not limited to flash thermography, ultrasonic testing, eddy current testing, microwave testing, shearography, and infrared testing.

10 Claims, 23 Drawing Sheets

| ITEM | QTY. | PART NO. | DESCRIPTION |
|---|---|---|---|
| 1 | 1 | E | Drawing Template E |
| 2 | 1 | F | Drawing Template F |
| 3 | 1 | G | Drawing Template G |
| 4 | 5 |  | Fastener |

| Test | Description per Table 5 |
|---|---|
| V | Uncoupled $2^{nd}$ & $3^{rd}$ layer |

Panel Tested per Table 5:
Flat panel #'s: 20, 21, 22, 43, 44, 45, 65, 66, 67

| TITLE | Assembly Template EE |
|---|---|
| DESCRIPTION | Uncoupled $2^{nd}$ & $3^{rd}$ Layer |
| DRAWN BY | PECINAJ |
| DATE | 7/09/2004 |

Scale: *Not to scale*

PROCESSES TO CREATE DISCRETE CORROSION DEFECTS ON SUBSTRATES AND ESTABLISH CORROSION NDI TEST STANDARDS

CROSS-REFERENCE TO RELATED APPLICATIONS

This application is a divisional application claiming priority to copending U.S. patent application Ser. No. 11/713,886, filed on Mar. 5, 2007, and claiming priority to U.S. Provisional Patent Application No. 60/779,265, filed on Mar. 3, 2006 and now expired. Those applications are incorporated by reference herein in their entirety.

BACKGROUND OF THE INVENTION

1. Field of the Invention

Embodiments of the invention relate to the fields of nondestructive inspection (NDI) and/or nondestructive testing (NDT) of substrates for corrosion. Preferably embodiments relate to a process for creation of discrete corrosion defects on substrates and to creation of standards for NDI and NDT. Hereinafter "NDT" will refer to uses for both NDI and NDT, unless otherwise indicated.

2. Background

Painted or coated substrates, including those substrates constructed from traditional steel and aluminum alloys as well as more modern composite and sandwich structures, present particular challenge for analysis by traditional NDT methods. For convenience, and unless otherwise noted, "paint" shall be used herein to refer to both paints and coatings when used as any part of speech. For painted parts or components, corrosion does not generally become evident until it has progressed far enough to disrupt the integrity of the paint. If the paint has not been disrupted but corrosion is still suspected to have begun at the surface of the substrate, identification of corrosion has required removal of the paint or other coating. Some methods that may be used to detect corrosion, such as hammering an area and listening for sounds characteristic of possible corrosion, is subjective and may be unreliable and/or may require a high amount of training and skill.

Whether the corrosion is discovered following disruption of the paint or after intentional removal of the paint, the paint must be removed and the substrate/substructure repaired and repainted after the corrosion damage has been repaired. Paint removal and replacement results in significant downtime, and it can generate significant hazardous waste, such as volatile chemicals and air pollutants.

It would be desirable to develop NDT corrosion test standards which emulate specific substrates, coatings, and substrate orientations for each application of interest. These NDT corrosion test standards could provide benchmarks for calibration of NDT systems, providing reliable and reproducible results for indicating corrosion damage and delineating corrosion damage from other mechanical defects under paint.

SUMMARY OF THE INVENTION

Embodiments of the invention provide a process to create NDT corrosion test standards in the laboratory. An NDT corrosion test standard is comprised of a substrate containing one or more known corrosion defects, where the substrate and corrosion defect is covered with paint. Preferably the paint is primer and topcoat, though other coating types and layers may be used depending on the application of interest.

Embodiments of the invention also provide a process to create discrete corrosion defects on an substrate. Discrete corrosion defects may be created by providing a substrate, masking the substrate with a substance that will limit corrosion to one or more selected areas during accelerated corrosion of the substrate. Preferably this substance is tape, preferably a polypropylene tape that will facilitate temporary masking and leave no adhesive residue when removed subsequent to creating corrosion defects, and that has been scored to remove areas where corrosion and/or mechanical defects are desired. These areas may be of varying size and shape, though circular areas are preferred so that a known depth to diameter ratio for corrosion and mechanical defects may be established.

Corrosion defects are created by immersing the substrate in a simulated or natural seawater or saltwater bath and using the un masked substrate surface areas as an anode for the application of current; this creates corrosion defects in the areas not covered by masking. Mechanical defects, if desired, are then created which have the same unit volume as the corrosion defects they were created from by removing the corrosion products by media blasting or another method known to those skilled in the art. The masking is removed, and one or both sides of the substrate are coated. More than one layer or type of coating may be applied. The coated substrate can then be subjected to environmental stresses such as but not limited to ultra violet and moisture in accelerated laboratory exposure testing or naturally occurring outdoor environmental exposure for an effective amount of time. These stresses may be applied, for example, to duplicate environmental effects on the substrate. For example, the coated substrate may be exposed to a Xenon arc to simulate sunlight, or it may be soaked in fresh or salt water to simulate a rain forest or oceanic environment.

Following stress of the coated substrate, the coated substrate is considered to be an NDT corrosion test standard which can be used 1) for evaluating the detection threshold and sensitivity of an NDT method to and/or 2) used in conjunction with an NDT method for corrosion NDI inspection and characterization of a filed application having similar substrate and coating materials of construction. Results of the NDT are correlated to the known corrosion and/or mechanical defects created by the above process. The NDT may then be used on other products and the results compared with those obtained during testing. In this way a user of the NDT may determine if similar corrosion exist under a coating when the NDT is used to test the same substrate/coating combination on a product or asset that has been subjected to filed service.

Optionally, prior to creation of the corrosion and/or mechanical defects, the substrate is formed into a shape closer to that of the eventual product to be tested. For example, if the ultimate product to be tested is an airplane wing bent at a fixed angle, the substrate may be bent. Substrates may also be welded, riveted, adhesively bonded or otherwise assembled at any point in the process.

Further embodiments of the invention provide a method for characterizing NDT methods by such criteria as their detection limits, environmental influences, and types of detected stresses by first creating known corrosion defects and/or other defects in the substrate to provide a known baseline for an NDT method, then evaluating the NDT method.

One or more NDT methods may be evaluated including, for example, but not limited to ultrasonic testing, flash thermography, eddy current testing, microwave testing, shearography, radiography and infrared testing. Substrates useful in the invention include but are not limited to aluminum and aluminum alloys, steel, and steel alloys. The substrate used in a particular NDT corrosion test standard will be determined by the item to which the test results obtained using the test standard will be applied. A substrate should be electrically conductive for the installation of corrosion defects to be successful. Paints suitable for use in the invention include but are not limited to epoxy, acrylic, urethane, latex paints, enamels, and other organic and inorganic coatings. In a preferred embodiment both a primer and a topcoat will be applied.

DETAILED DESCRIPTION OF THE INVENTION

Processes described herein allow evaluation of nondestructive testing of corrosion and non-corrosion defects under paint (or other coatings) and on the backside of a metal substrate. Suitable substrates include, for example, but are not limited to heat treatable and non-heat treatable aluminum alloys, carbon steels, and alloy steels. Testing standards may be developed, for example, for rotor-wing aircraft, fixed wing aircraft, ground vehicles, ships, vessels, storage structures, dwellings, highways, bridges, and other and transportation structures.

In a preferred embodiment, test standards are developed for substrates of varying thicknesses typical of the field application of interest (in the initial development of this intellectual property substrate thicknesses of 0.030" to 0.060" were used), with other varying physical properties, including curvature (or lack of curvature), use of adhesive between two or more layers of substrate, and use of mechanical bonding (for example, rivets) of two or more layers of substrate. In preferred embodiments defects range in depth and diameter typical of the field application of interest (in the initial development of this intellectual property defect depths ranging from 0.0005" to 0.006" and diameters from 0.062" to 2.75" were used). Corrosion defects (and the similar unit volume mechanical defects created by removing the corrosion products of select corrosion defects) may be installed on the surface of the substrate under the paint, or on the (unpainted or painted) backside of the surface, or both.

Figure 1:
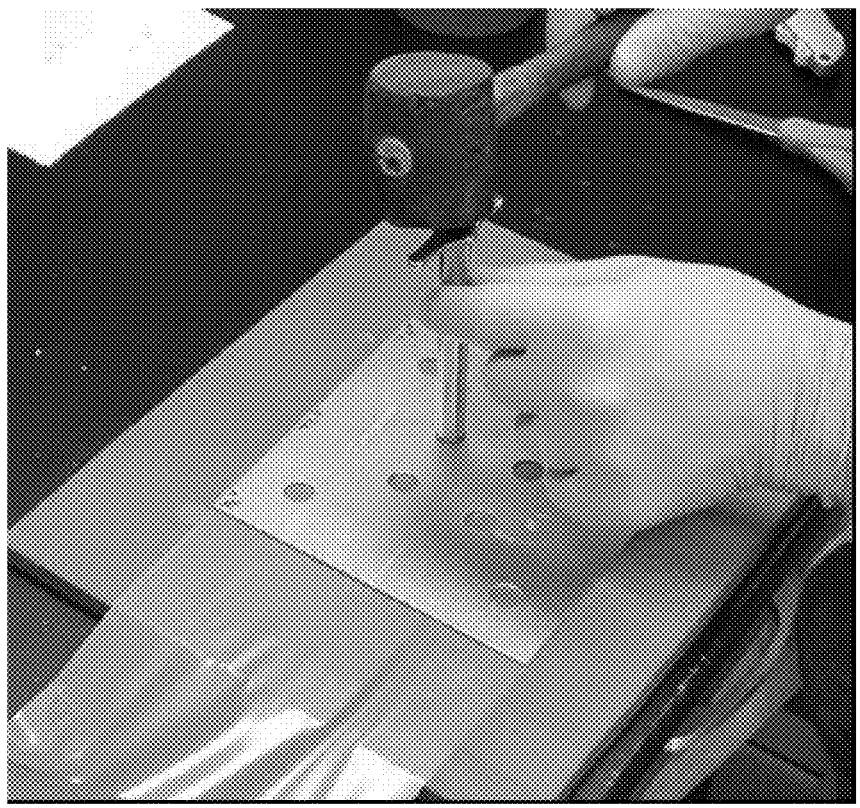
FIG. 1 shows a masking material being punched with holes for creation of discrete corrosion defects of selected sizes and locations.
Figure 2:
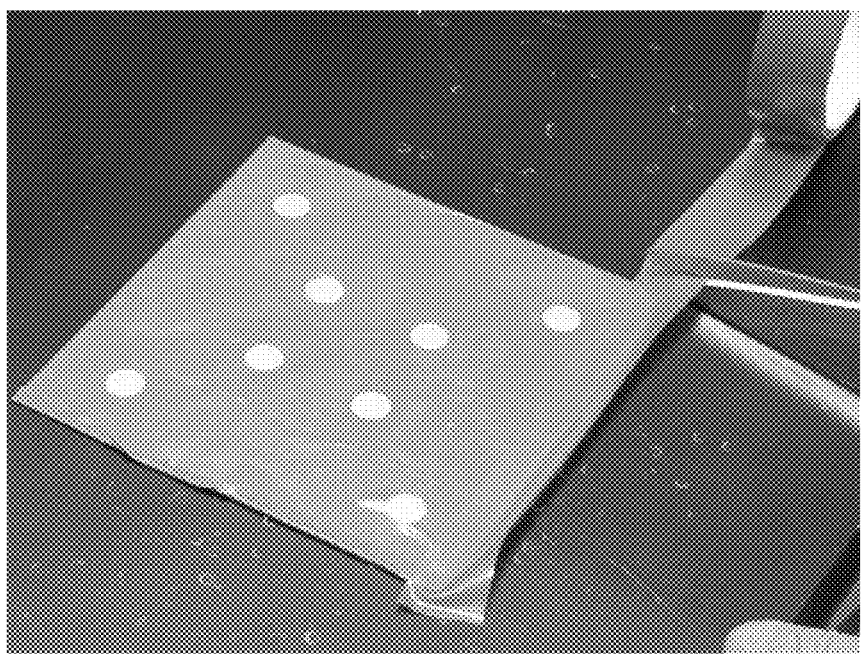
FIG. 2 shows an aluminum substrate affixed to masking material of FIG. 1.
Figure 3:
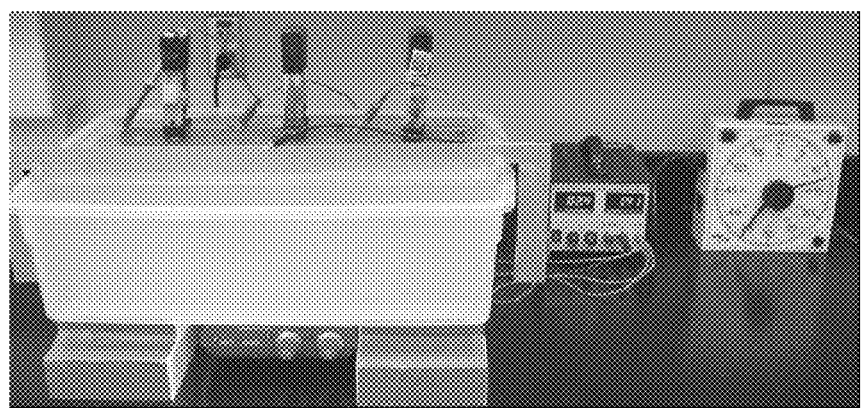
FIG. 3 shows an apparatus used to create discrete corrosion defects according to the invention.
Figure 4:
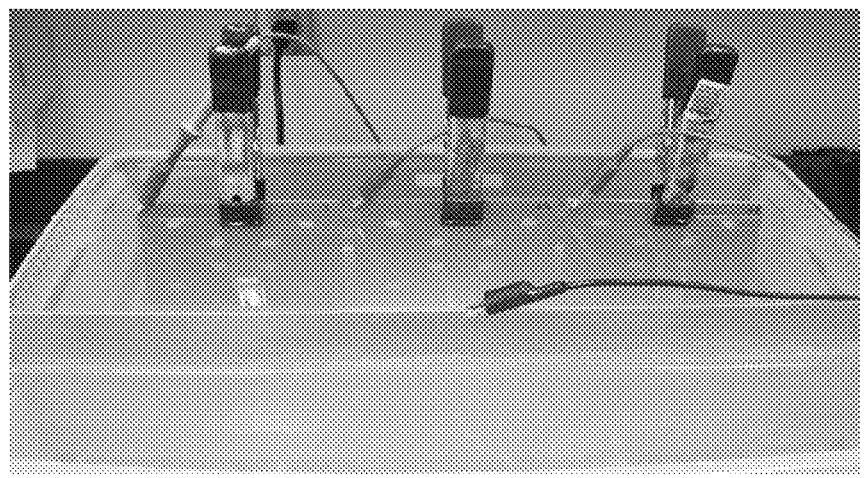
FIG. 4 shows a close-up view of an aluminum substrate covered with masking material (from FIG. 3) during electrolytic processing.
Figure 5:
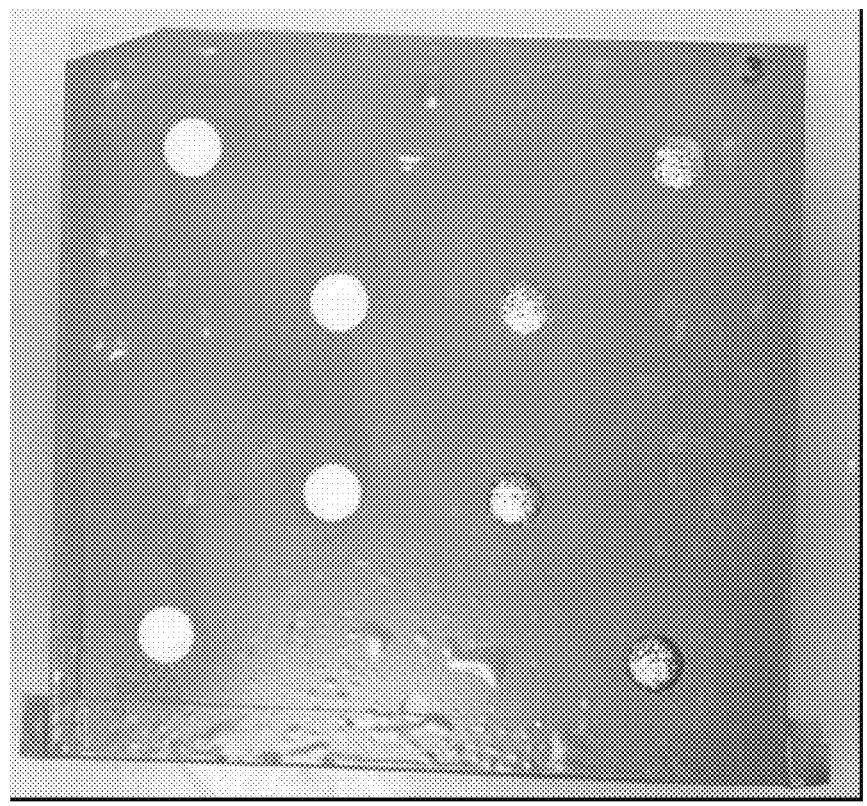
FIG. 5 shows discrete non-corrosion defects being created by removal of corrosion defects with a blasting media.

In one embodiment of the invention, the discrete corrosion defects are created by the following process. First, the desired diameters and locations of corrosion and non-corrosion defects are cut into a masking material. Use of a template and a cutting took to cut holes in a masking material is shown in FIG. 1. The masking material is affixed to a substrate to be processed, and the sides of the material are also covered by masking material. A substrate bearing a masking material is shown in FIG. 2.

A variety of masking materials may be used. A masking material should allow the corrosion to be localized to the desired areas on the substrate, but otherwise selection of a masking material is at the discretion of the operator. Criteria used to select an appropriate masking material will include durability during the corrosion process, ability to adhere to the substrate, and ability to prevent corrosion defects in areas where they are not desired. In a preferred embodiment, the masking material is a polypropylene tape. In other embodiments, the masking material is selected from, but not limited to discrete rubber like masking components clamped to the surface, paint, or other non conductive materials.

The unmasked surface areas of one or more substrates bearing the masking material become the anode in a circuit. Any corrosion-resistant material can be fabricated and used as the cathode in the circuit. This may include, for example, aluminum alloy or stainless steel. A DC power supply (or equivalent battery) is used to power the process by impressing a specific current. Electrical continuity is made from the positive terminals of the power supply to the anode and from the negative terminals to the cathode. The circuit is completed by submerging the cathode and anode(s) in a seawater or saltwater electrolyte.

To develop discrete corrosion defects on aluminum substrates, the power supply is set for a target optimized current density of about 0.20 to about 0.50 Amps/square inch of total defect area and energized for process duration in the range of about 10 to about 90 minutes, with greater desired defect depth requiring greater time. To develop discrete corrosion defects on steel substrates, the power supply is set for a target optimized current density of about 0.01 to about 0.05 Amps/square inch of total defect area and energized for a process time of about 90 to about 180 minutes (again, depending on desired depth), and the pH of the seawater or saltwater electrolyte can be modified with acid to lower the pH. Slight reduction of the pH of the electrolyte promotes the formation of more tightly adhered iron oxide corrosion products.

Principal corrosion products formed during the electrolytic process are a metal oxide of the substrate or, in the case of an aluminum alloy, aluminum oxides or alumina. If the substrate is steel, the products of the electrolysis are iron oxide.

Figure 6:
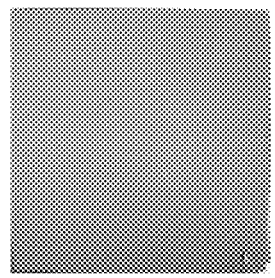
FIG. 6 shows an unpainted test substrate with discrete non-corrosion defects (left side) and discrete corrosion defects (right side).
Figure 6:
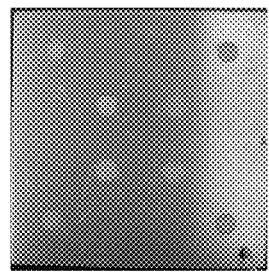
Figure 7:
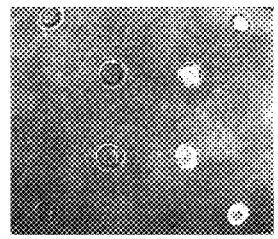
FIG. 7 shows the same test substrate as FIG. 6, except the substrate is painted, hiding the discrete corrosion defects.

An example of an unpainted aluminum alloy substrate corrosion NDT test standard containing discrete corrosion and non-corrosion defects is shown in FIG. 6. FIG. 7 shows the same test standard after it has been primed and painted, and it should be noted that the defects are practically invisible.

Discrete non-corrosion defects of the same unit volume as the discrete corrosion defects may be created following creation of the discrete corrosion defects. For instance, one might use an media blasting process to remove the corrosion products, leaving an indentation or hole in the treated substrate where the corrosion products were previously formed. One might also pre-treat the substrate with an media blasting process to promote the formation of corrosion products, then mask the abraded area to prevent corrosion in the masked areas.

Following creation of the discrete corrosion and non-corrosion defects, the masking material is removed and the substrate is painted or otherwise coated. Optionally, the painted or coated substrate is further environmentally stressed to simulate coating degradation. For example, a painted substrate may be immersed in fresh water, saltwater, or other chemicals for a period of time to simulate marine, rural, or industrial atmospheres. A painted substrate may also be treated with a xenon arc or artificial ultraviolet lamination to simulate sunlight. One might further treat the substrate in the presence of moisture at high or low temperature. In a further embodiment, environmental stresses may be alternated to simulate even more severe environments.

Following creation of defects, painting the substrate, and, optionally, exposure of the painted substrate to environmental stresses, a corrosion NDT test standard is considered to have been created. The corrosion NDT test standard can then be used with an NDT method of choice. Suitable NDT methods include, but are not limited to, ultrasonic testing, flash thermography, eddy current testing, microwave testing, shearography, and infrared testing. The corrosion NDT test standards can be inspected using one or more NDT methods. Inspection data is collected using one or more NDT methods. The data is then analyzed to characterize the corrosion detection threshold and sensitivity of each NDT method of interest and create a library of results for corrosion NDT test standards to be used for later comparison of data collected and analyzed on a product or field application. Field tests using the NDT methods on similar substrates with similar paints and/or coatings (preferably the same substrates with the same coatings) may then be compared with the standards developed from the controlled corrosion NDT test standard evaluation.

Figure 8:
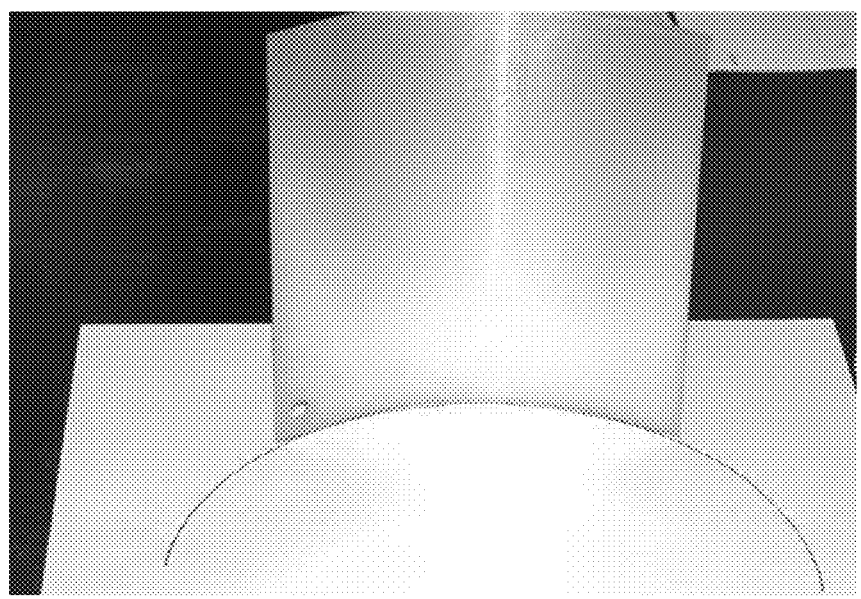
FIG. 8 shows nondestructive flash thermography results detecting discrete corrosion defects (white, right) and discrete non-corrosion defects (dark, left) in the painted substrate of FIG. 7. Seeing similar results in a field test would indicate that the painted object likely needed stripped, repaired, and repainted.

FIG. 8 shows the test standard of FIG. 7 imaged with flash thermography, a nondestructive investigation technique. The discrete corrosion defects are shown in white, under the paint, and the discrete non-corrosion defects are darker. Analysis of corrosion defects allows comparison of aspect ratio and geometry expected from the known defects that were created. This may be used to tune the actual results obtained by the NDT.

Embodiments of the invention allow effective field and laboratory use of nondestructive testing for detection of corrosion. In general, test standards are developed and used according to the following process. First, a subject for NDT is identified. For example, the subject may be a bridge, or a fleet of aircraft, watercraft, or ground vehicles. All members of the subject class should be constructed from the same substrate material and painted with the same paint (or, for example, the same primer/topcoat combination). Likely areas of corrosion are determined, and the chemistry and morphology of the corrosion products of the area to be detected for corrosion is characterized. Characterization of physical geometry and structural design of the area to be tested (flat or curved, if it has ridges or other elevations, or if it has overlapping substrates connected by adhesives, welding, or mechanical assemblies) shall be identified. The substrate to be tested may have a uniform thickness, or the thickness may vary. The substrate may be supported by a strut or substructure.

After the area to be tested is characterized, material with a composition identical to the substrate is procured, and the assembly is duplicated on a small scale. For example, curves, ridges or elevations may be added, or two or more pieces of a substrate may be welded, adhered, or connected. Corrosion defects are then created as described elsewhere in this disclosure. To develop the process to create discrete corrosion defects in the laboratory, the process should be developed in such a manor to develop corrosion products with similar chemistry and morphology as the specific application of interest.

Following creation of one or more corrosion defects and, optionally, mechanical defects, the material is painted using the same materials as the intended NDT subject. For example, if the subject has a topcoat and primer of a particular composition, that topcoat and primer are also applied to the material. This creates a corrosion NDT test standard for that particular substrate and paint combination. Ideally, multiple corrosion NDT test standards are created with different corrosion patterns and amounts.

In a preferred embodiment, one or more duplicates are made of each test standard. One test standard from each set of duplicates may be used as control, while the others may be subjected to real or simulated environmental stresses as described elsewhere in this disclosure.

After the corrosion NDI test standards have been created using a particular substrate and paint combination, then are tested using one or more NDT methods that may be applied to the originally selected field subjects. Data from these tests is collected and stored. Performance of multiple non-destructive tests on multiple standards allows optimization of analysis by each NDT method. If desired, test standards may be created that have corrosion defects or mechanical defects of sizes and/or densities at or below the effective detection range of the selected NDT method. This allows confirmation of the detection range and optimization of the NDT to be as near to that value as possible.

After the data from NDT of the corrosion NDI test standards has been collected, field testing of the originally selected subjects is conducted using the same NDT method(s). Data from the field subjects is compared to the data from the test standards, allowing an operator to determine with confidence if corrosion or mechanical defects exist in the test subject.

Corrosion NDI test standards created using a particular substrate and a particular paint are most effective (and in some cases, only effective) for comparison with field subjects that have the same substrate material and paint composition. If testing of a different substrate material and/or paint is desired, different corrosion NDI test standards may be constructed and corroded as described herein, and those test standards may be analyzed with NDT methods and the data collected.

EXAMPLES

The following examples are intended to guide those skilled in the art in the practice of this invention. The scope of the invention, including the creation of corrosion NDI test standards with varying geometry, substructure, primer, topcoat, substrate material, or NDT material, should not be construed to be limited by these examples, which describe creation of a particular set of corrosion NDI test standards and use of those test standards to collect and analyze data for a particular field subject.

Example 1

Preparation of Aluminum Test Panels

Figure 9:
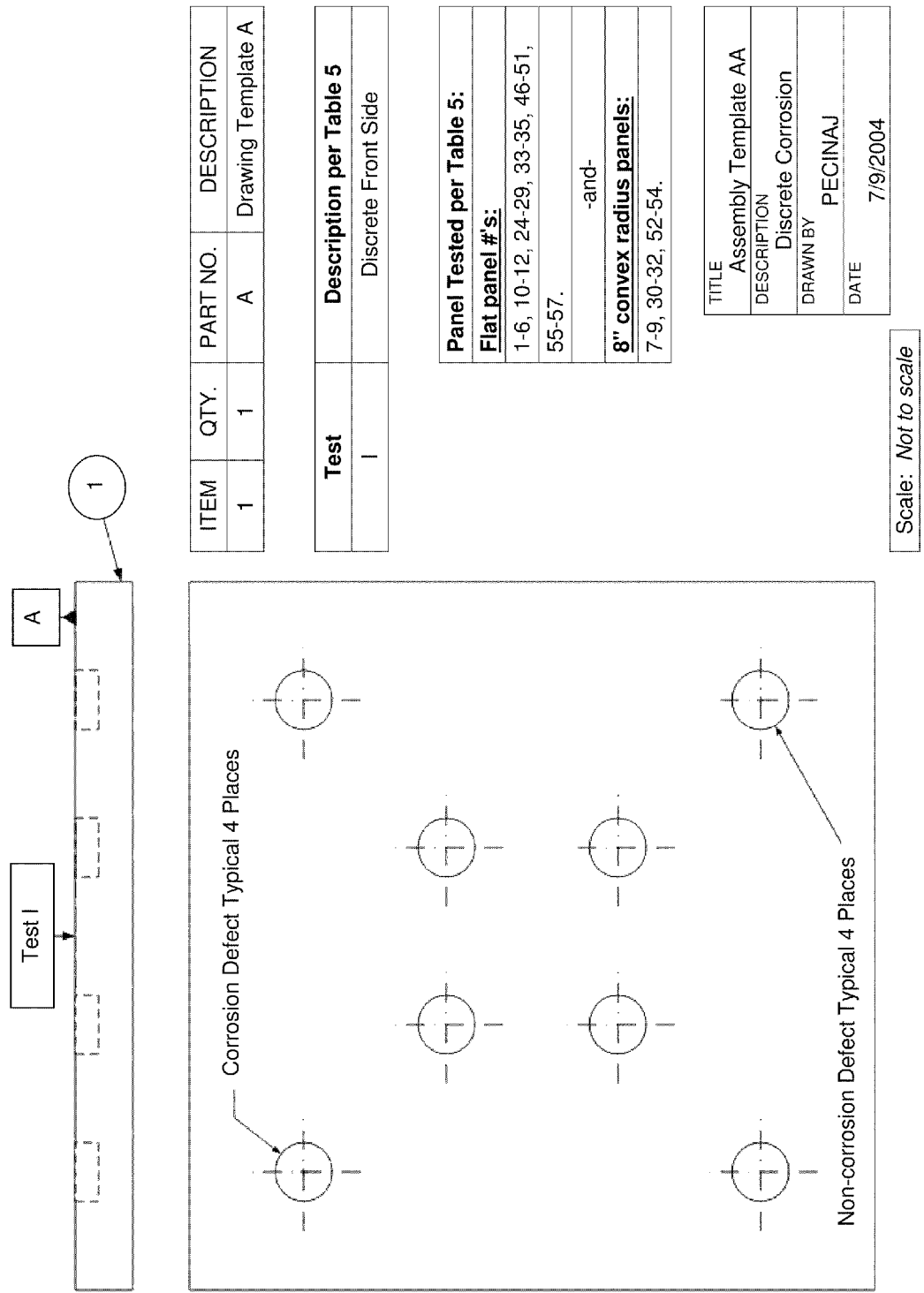
FIG. 9 shows formation of an 8" radius aluminum panel as described below in Example 1.
Figure 10:
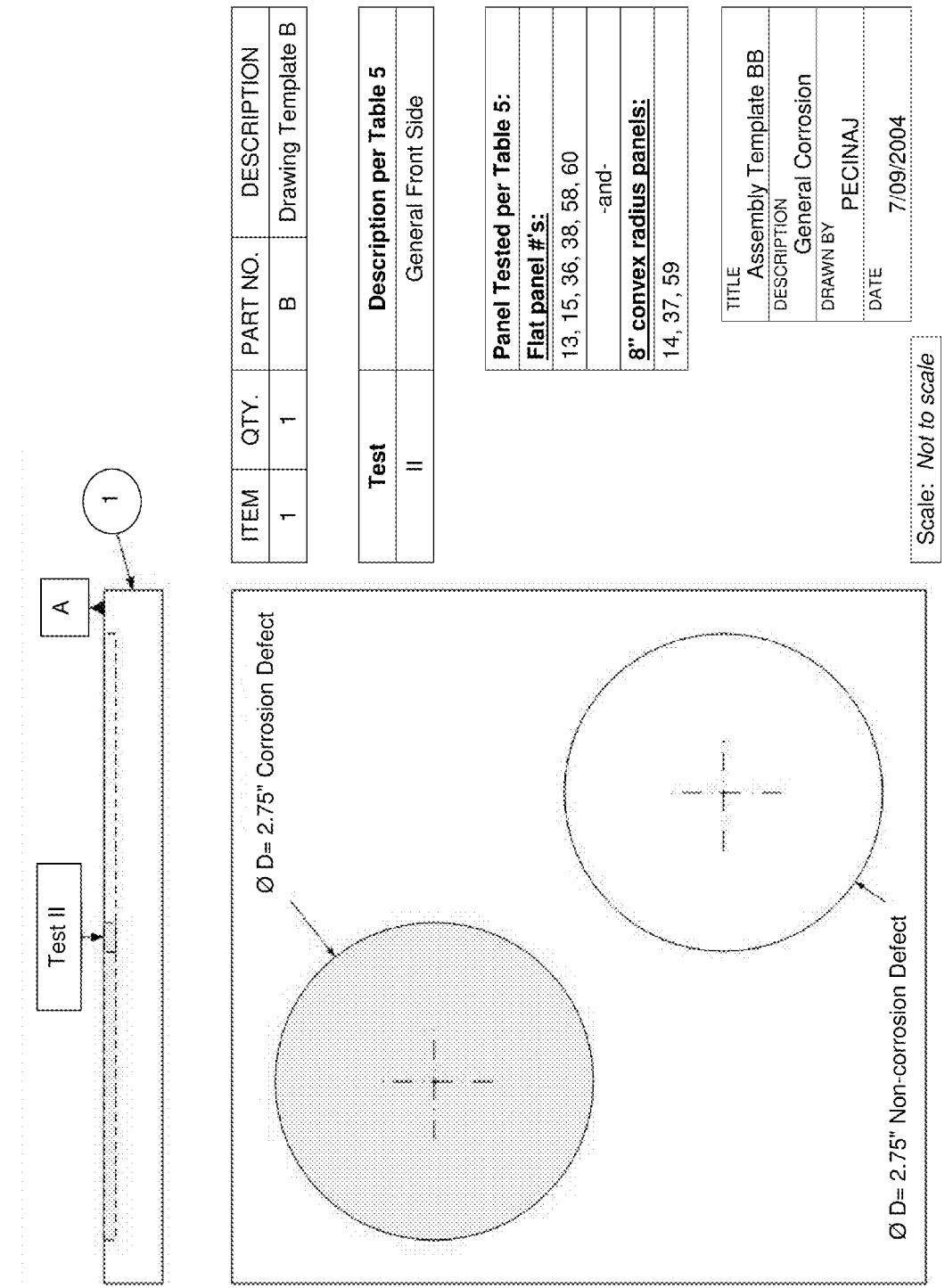
FIGS. 10-16 show a variety of masking templates prepared as described in Example 1.
Figure 11:
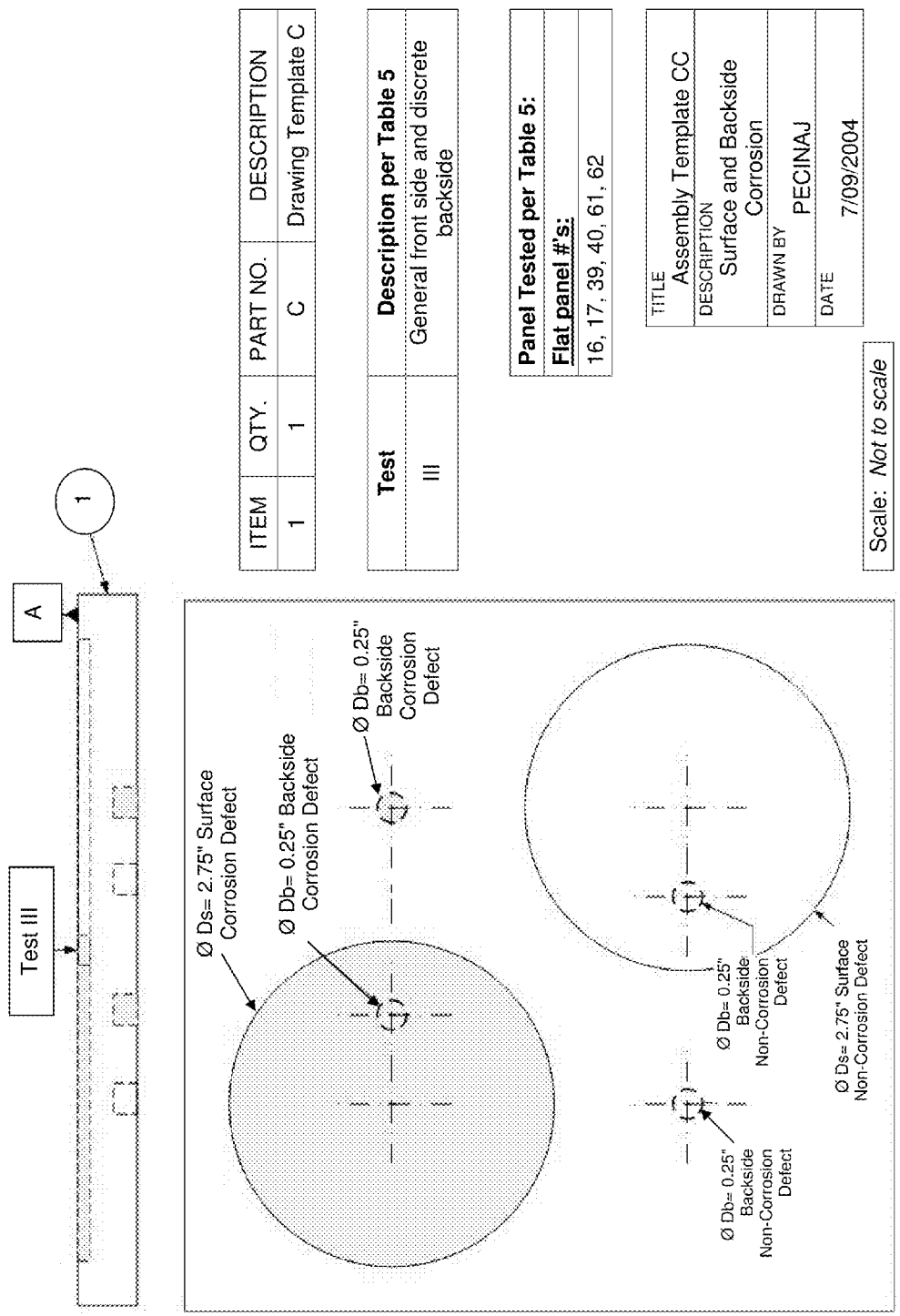
Figure 12:
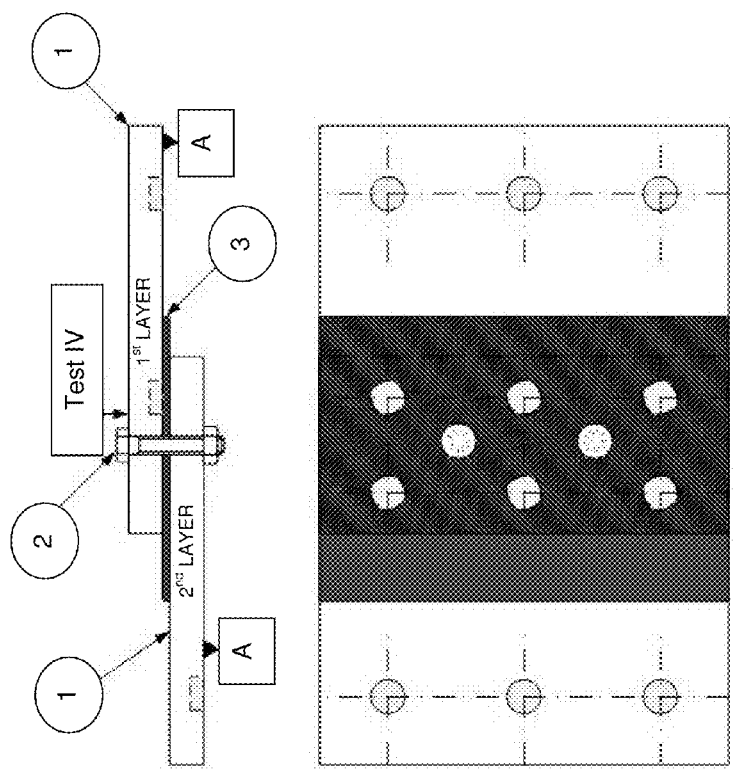
Figure 13:
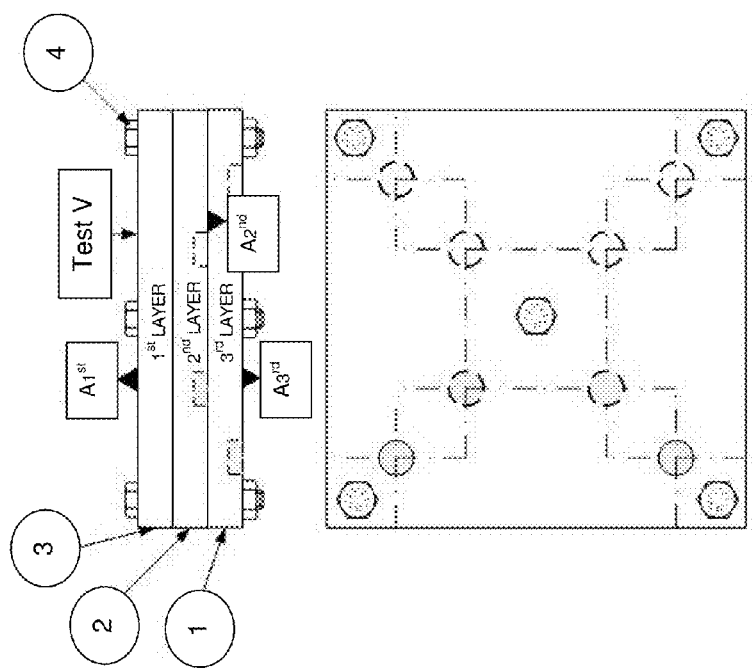
Figure 14:
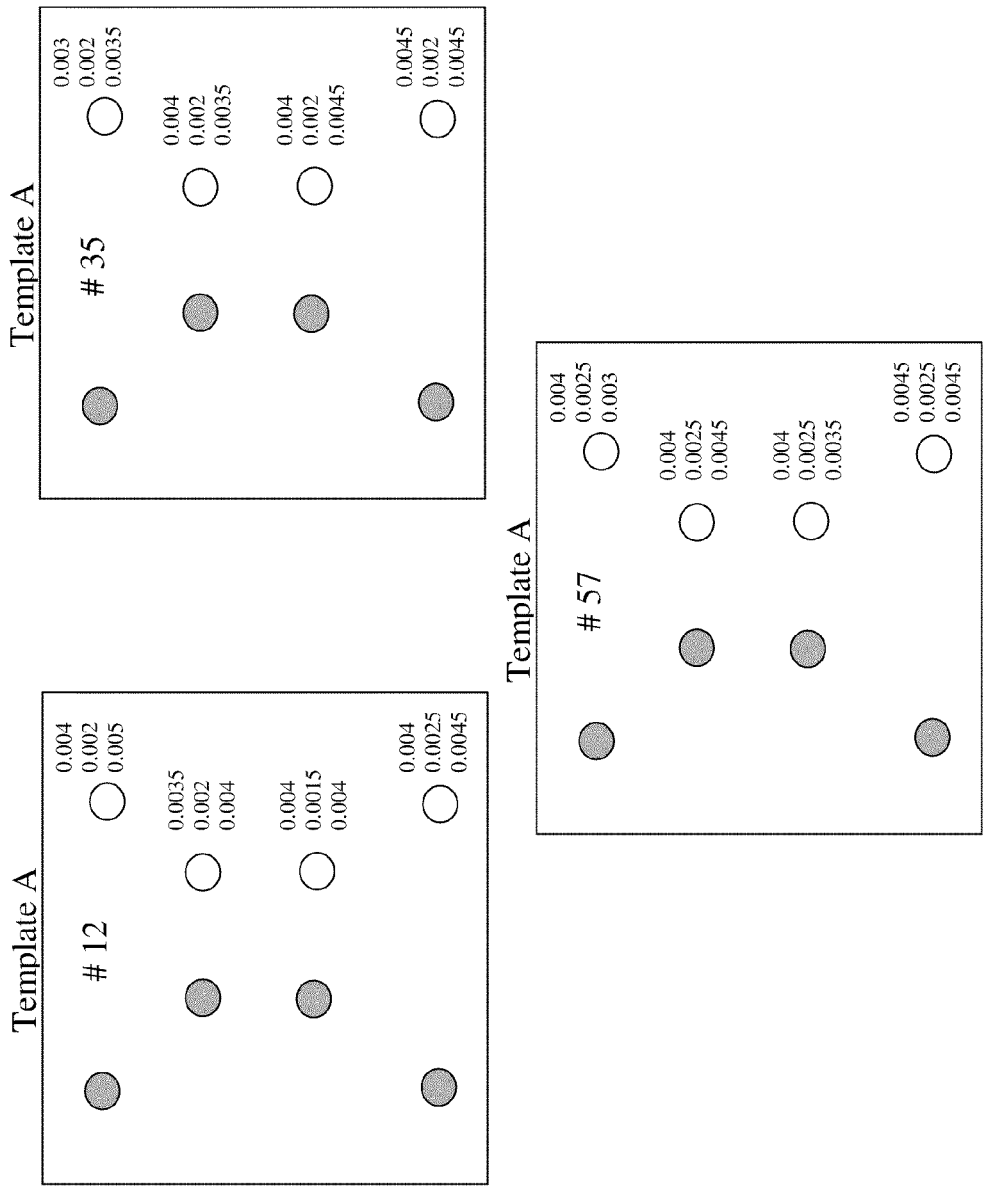
Figure 15:
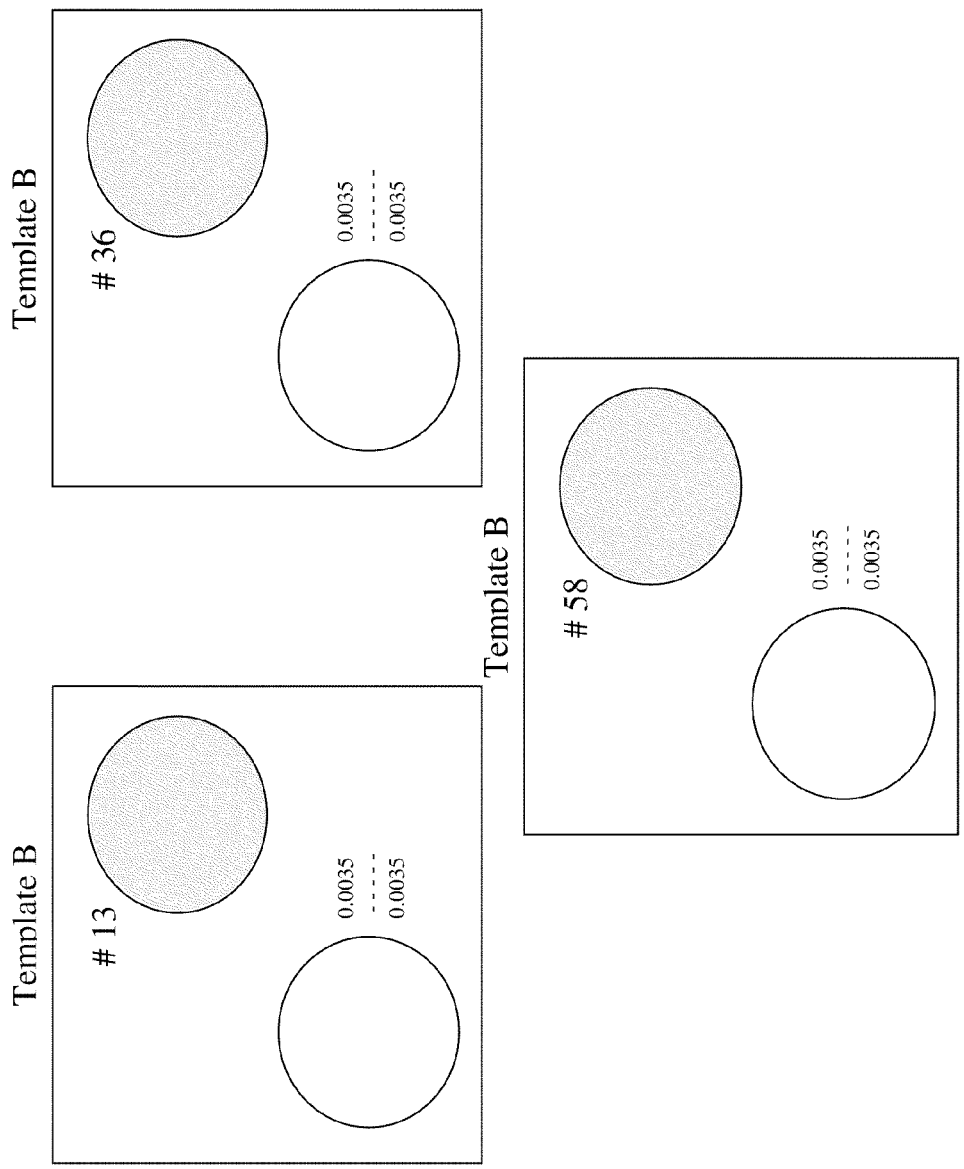
Figure 16:
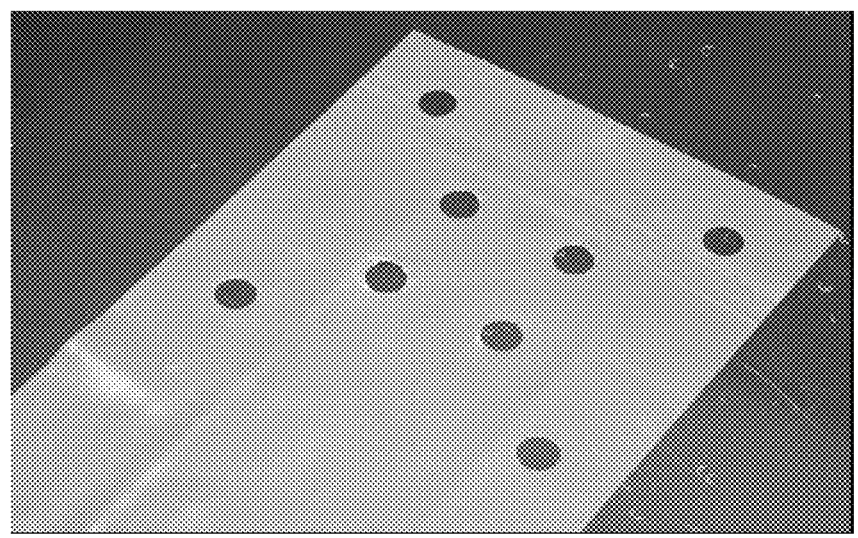

A number of 2024-T3 aluminum alloy test panels with thicknesses of both 0.032" and 0.063" and cut to 6"×6" were purchased from Alro Metals Service Center in Tampa, Fla. Wavelength dispersive X-ray fluorescence was used to confirm that the panels were 2024 aluminum alloy. Because an 8" panel radius was desired, panels were formed over a 2" schedule 40 PVC mandrel, then compared to an 8" radius template and adjusted to fit. Formation of the panel with the appropriate radius is shown in FIG. 9.

Figure 17:
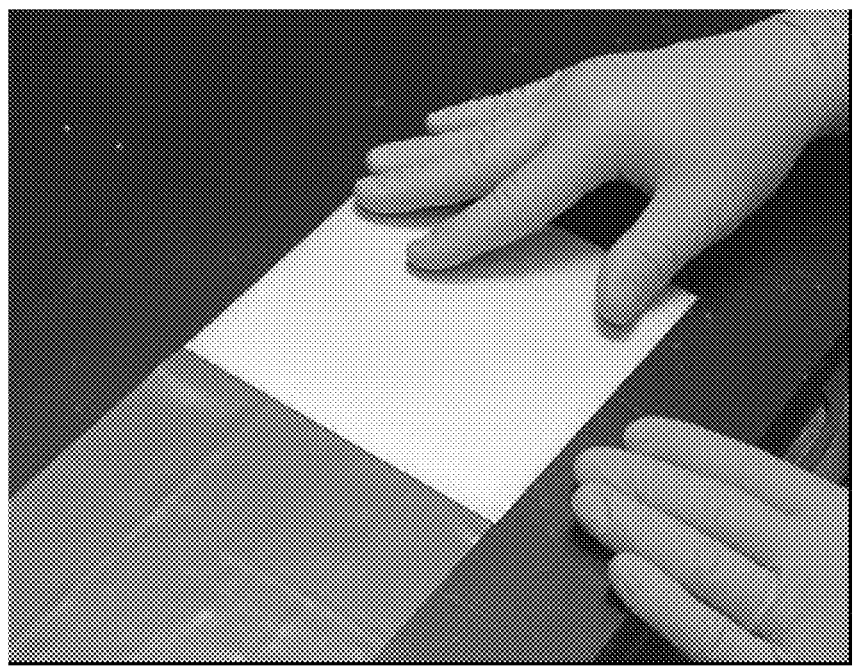
FIG. 17 shows the masking tape of FIG. 9 including punched holes.
Figure 18:
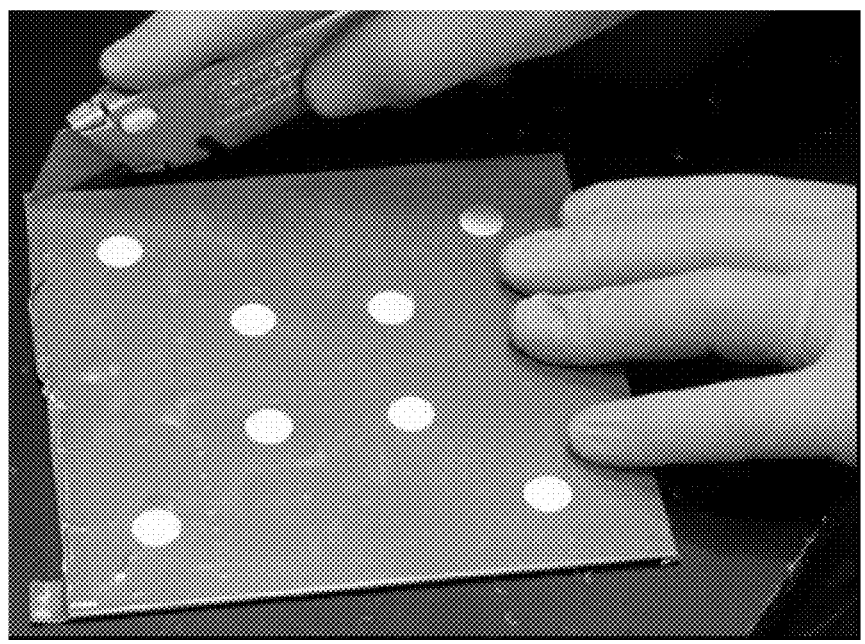
FIG. 18 shows an aluminum test panel placed over the masking tape, as reported in Example 1.

Eight aluminum masking templates were prepared, each with different combinations of holes of varied sizes. Seven of these templates are shown as FIGS. 10-16. Rolls of 150T Preservation/Fine Line masking tape were purchased from Electrotape Specialties Inc., Odessa, Fla., in six inch and 1 in widths. The masking tapes were 7-mil thick plasticized polyvinyl chloride coated with an aggressive non-thermosetting rubber-resin adhesive. FIGS. 1, 17, and 18 show the masking of one aluminum panel. As shown in FIG. 1, masking tape was placed on a rubber surface under a template. Holes were punched in the masking tape according to the template. FIG. 17 shows the masking tape with the punched holes. FIG. 18 shows the aluminum test panel placed over the masking tape.

Figure 19:
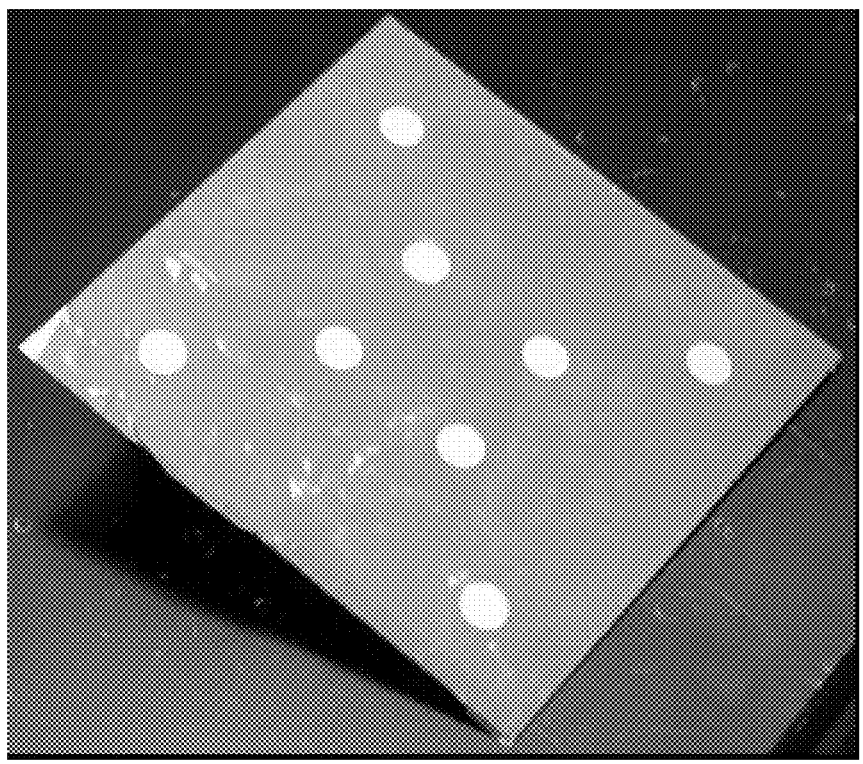
FIG. 19 shows a masked aluminum substrate with a cutout for contact with the anode connector.

The back of a wooden brush was used to apply pressure to the masking tape. Attention was given to the areas around the holes, to provide a liquid-tight seal. Pockets of air between the holes were permitted. One side of the aluminum test panel were masked with masking tape that included holes punched according to the same template. The edges of the test panel were also masked with one inch wide masking tape. Masking tape was then removed from one corner of the test plate to expose the aluminum for future electrical conductivity needs. A completely masked aluminum test panel with a corner cut-out is shown in FIG. 19.

Glass bead blasting was then applied to remove the chromate conversion coating in the defect areas. Blasting was accomplished using the "Barrel Blaster" manufactured by Lake Buchanan Industries Inc. Removal of the chromate conversion coating gave the unmasked areas the lowest surface resistance possible, allowing a consistent current density in subsequent operations. Glass Bead media of 100/120 screen size was used with a regulator pressure of 60-70 psig at a nozzle-to-panel distance of about four inches. Loss of yellow color of the chromate coating indicated that it had been removed and that blasting could cease. Usually this took about 10 seconds.

Example 2

Creation of Corrosion Defects

An electrolytic process was used to create discrete corrosion defects on 2024 aluminum. The process utilized a masked aluminum substrate panel prepared according to Example 1, a 32 quart capacity plastic tank containing a natural seawater electrolyte stirred with a Corning Stirrer/Hotplate Model PC-420, a cathode constructed from 6061-T6 aluminum alloy (per ASTM B209M) as the cathode material, and an Electro Industries model DIGI 35A, 0-30 Volt/3 Ampoutput regulated power supply controlled by a GraLab timer model 171 (Dimco Gray Co., Centerville, Ohio) as a constant current source.

The stirrer was set on 10, and the hotplate was off. The natural seawater was obtained from the Clearwater Marine Aquarium and was maintained at ambient temperatures ranging from about 71 to about 81° F. Approximately 30 quarts of electrolyte were discarded and replenished every 70 minutes of current flow. During processing the electrolyte temperature did not increase more than 1 degree above ambient temperature.

The aluminum cathode was submerged for a total exposed cathode area of about 220 square inches. Distance of the cathode to the test panel was about 7.5". For most runs, three test panels were immersed in the electrolyte and connected in parallel. This was done to allow three identical (or nearly identical) panels for a control group, simulated desert group, and simulated tropical group.

The setup described above was modified for creation of larger defects. For 0.062" diameter defects, a cathode with only 5 square inches of exposure was used, and the unmasked exposed surface of the test panel was oriented away from and positioned about 2" away from the exposed surface of the cathode. For larger defects, including 2.75" diameter defects, individual defects on each panel were processed consecutively to provide an adequate current density to create a defect.

Current and time were both varied to change the corrosion defect creation. Ideal current density of 0.3 Amps/square inch was established, and that value was used as a starting point for all other configurations.

Example 3

Creation of Non-Corrosion Defects

To creation non-corrosion defects, panels treated according to Example 2 were subjected to glass bead blasting as set forth in Example 1. Glass bead blasting was conducted at only selected corrosion defects, and ceased after all evidence of corrosion was removed from that particular defect. Non-corrosion defects and corrosion defects were then quantified for such features as size and depth.

Example 4

Painting Substrates

Substrates treated according to Examples 1 through 3 were primed with a strontium chromate-based inhibitor with a dry film thickness target of between 0.0006"-0.0009" on both surfaces. The substrates were then top-coated with a dry film thickness target of between 0.0018"-0.0020" on the exterior surface. Topcoat was flash cured in an over at 225° F. for seven minutes. Total film thickness in one run was about 0.0035", which was above the target thickness of 0.0024" to about 0.0029".

Example 5

NDT Results

Substrates prepared according to Examples 1-4 were tested with flash thermography. Thermography was performed using a Thermal Wave Imaging (TWI) Thermoscope DM IR NDI System. Tests were performed using the Echotherm 6 operating program, at a power level of 100%, a flash delay of 2.3 milliseconds, a pulse width of 3 milliseconds, a gate width of 10, 100 frames, the slope mode, a filter setting of "mean, 1×1, 1 cycle," no advanced frame settings, a flash frame of 10, and a number 2 primary gate for analysis.

Figure 20:
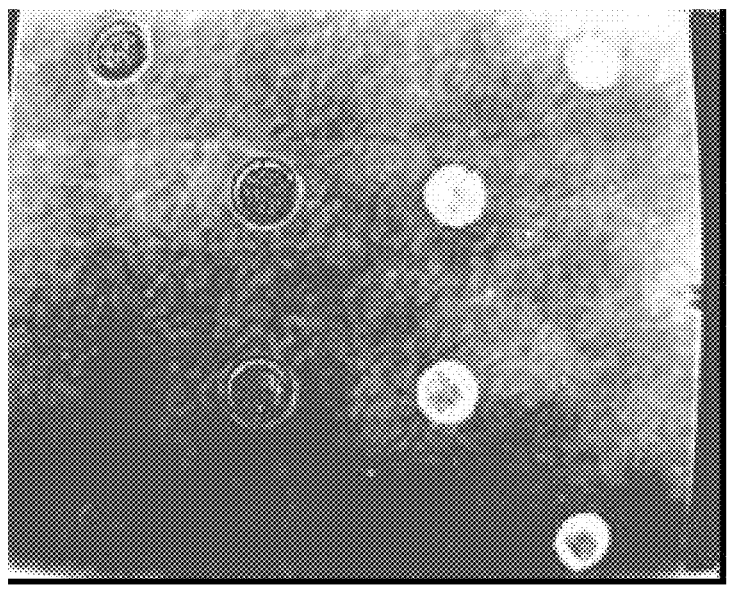
FIGS. 20-23 show examples of treated, painted substrates tested with flash thermography according to the invention.

FIG. 20 shows a typical test image. There are four mechanical defects on the left side of the specimen and four corrosion defects on the right side of the specimen. Both types of defects (mechanical and corrosion) are clearly visible, with the exception of the mechanical defect in the lower left corner of the image. The corrosion defects are clearly distinguishable from the mechanical defects, which could be important when checking previously treated areas. It was speculated that the corrosion defects appear much lighted than the surrounding area because the corrosion products tend to restrict the flow of heat into the inspection surface, whereas the mechanical defects only reveal a minor change in thermal properties when compared to the surrounding painted material.

Figure 21:
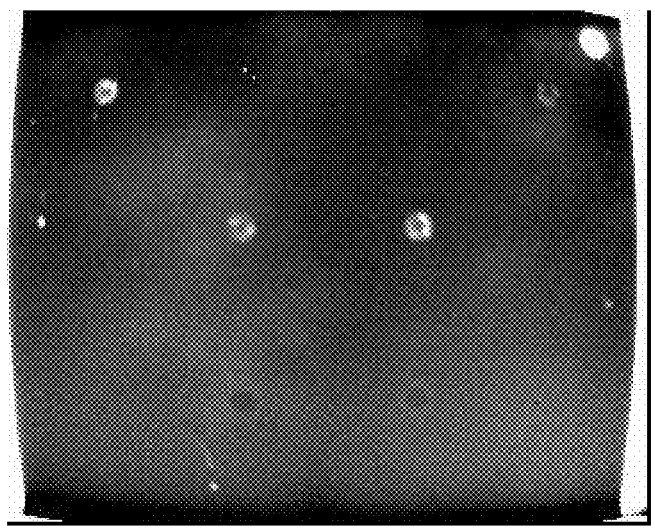

Further thermal imagery was taken. FIG. 21 shows another example of a specimen analyzed by flash thermography. In FIG. 21, corrosion defects are on top, while mechanical defects are on the bottom. Although the mechanical defects were different depths, they are all detected similarly.

Figure 22:
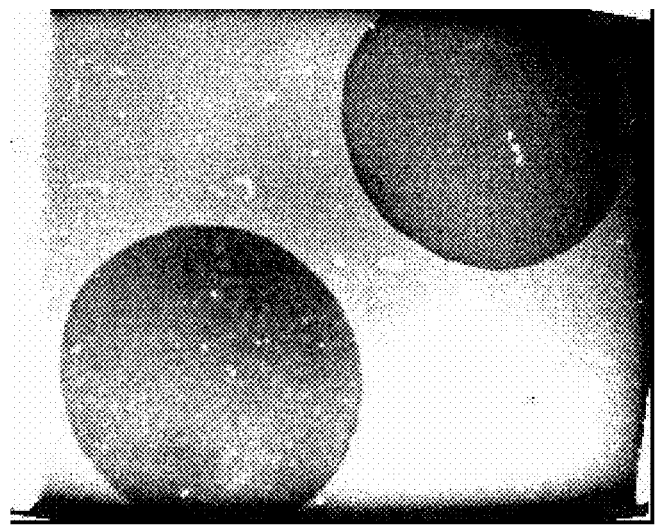
Figure 23:
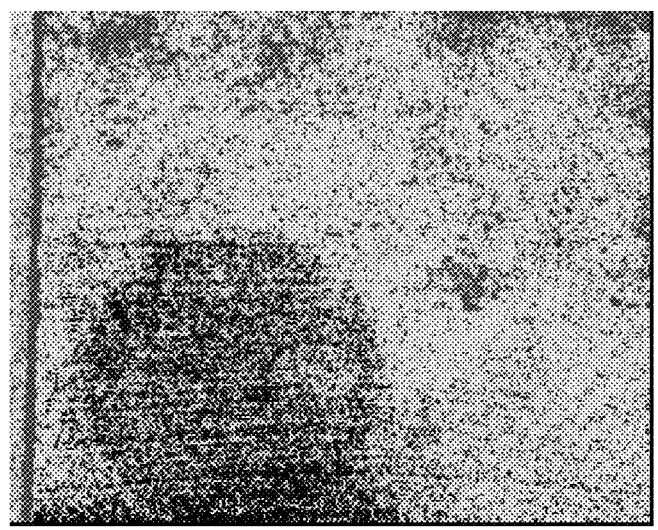

FIGS. 22 and 23 show the same test panel viewed under two imaging palettes. The corrosion defect is above the mechanical defect in this image. The ability to discern only the mechanical defect in FIG. 23 shows the ability to discern a mechanical defect from a corrosion defect by changing the color imaging palette of the thermography.

Whereas particular embodiments of this invention have been described for purposes of illustration, it will be evident to those persons skilled in the art that numerous variations of the details of the present teaching may be made without departing from the invention as defined in the appended claims. Those patents and publications discussed herein should be viewed as indicative of the level of skill in the art, though no admission is made that any document is a prior art reference. All of the foregoing patents and publications herein, including but not limited to those included in the background of the invention are hereby incorporated by reference. To the extent that the incorporated material conflicts with existing definitions, statements, or other disclosure material set forth in this description, the disclosure as explicitly set forth herein supersedes any conflicting material incorporated by reference.

As used herein, the singular forms "an," "a," and "the" used in the specification and claims include both singular and plural unless the content clearly dictates otherwise. While specific embodiments and examples of the invention are described herein, one skilled in the art will recognize that various modifications may be made without departing from the spirit and scope of the present invention as defined in the appended claims.

We claim:

1. A method for assessing at least one of corrosion under coating detection threshold, statistical reliability, and accuracy of a non-destructive testing system, comprising:
   a. providing at least one coated substrate, said substrate comprising at least one known corrosion defect;
   b. testing said coated substrate with a non-destructive testing system;
   c. collecting data from step (b);
   d. optionally, repeating steps (a) through (c) a plurality of times.

2. The method of claim 1, further comprising the step of optimizing said testing system after one or more iterations of steps (a) through (c).

3. The method of claim 2, wherein said optimization includes comparison of an expected aspect ratio and geometry based on the known defects.

4. The method of claim 1, wherein said known corrosion defect is known as to at least one property selected from the group consisting of size, shape, location, chemistry, and morphology of corrosion defect.

5. The method of claim 1, wherein said coated substrate is shaped to have a shape similar or identical to the shape of another object to be tested by said nondestructive testing system using said collected data.

6. The method of claim 1, wherein said substrate is made of a material selected from the group consisting of aluminum, aluminum alloy, steel, and steel alloy and a metal alloy subject to corrosion.

7. The method of claim 1, wherein said nondestructive testing system is selected from the group consisting of ultrasonic testing, flash thermography, eddy current testing, microwave testing, shearography, radiography, and infrared testing.

8. The method of claim 1, wherein said coating on said coated substrate is selected from the group consisting of organic coating polymers, epoxy, acrylic, urethane, latex, enamel paint, inorganic coatings, metals, alloys, ceramics, and combinations thereof.

9. The method of claim 1, wherein said data includes at least one of corrosion detection threshold and sensitivity of said nondestructive testing system.

10. The method of claim 1, said substrate further comprising at least one known mechanical defect.

* * * * *